Dec. 27, 1966 G. MERRILL Plant Pat. 2,694
PEACH TREE
Filed June 11, 1965
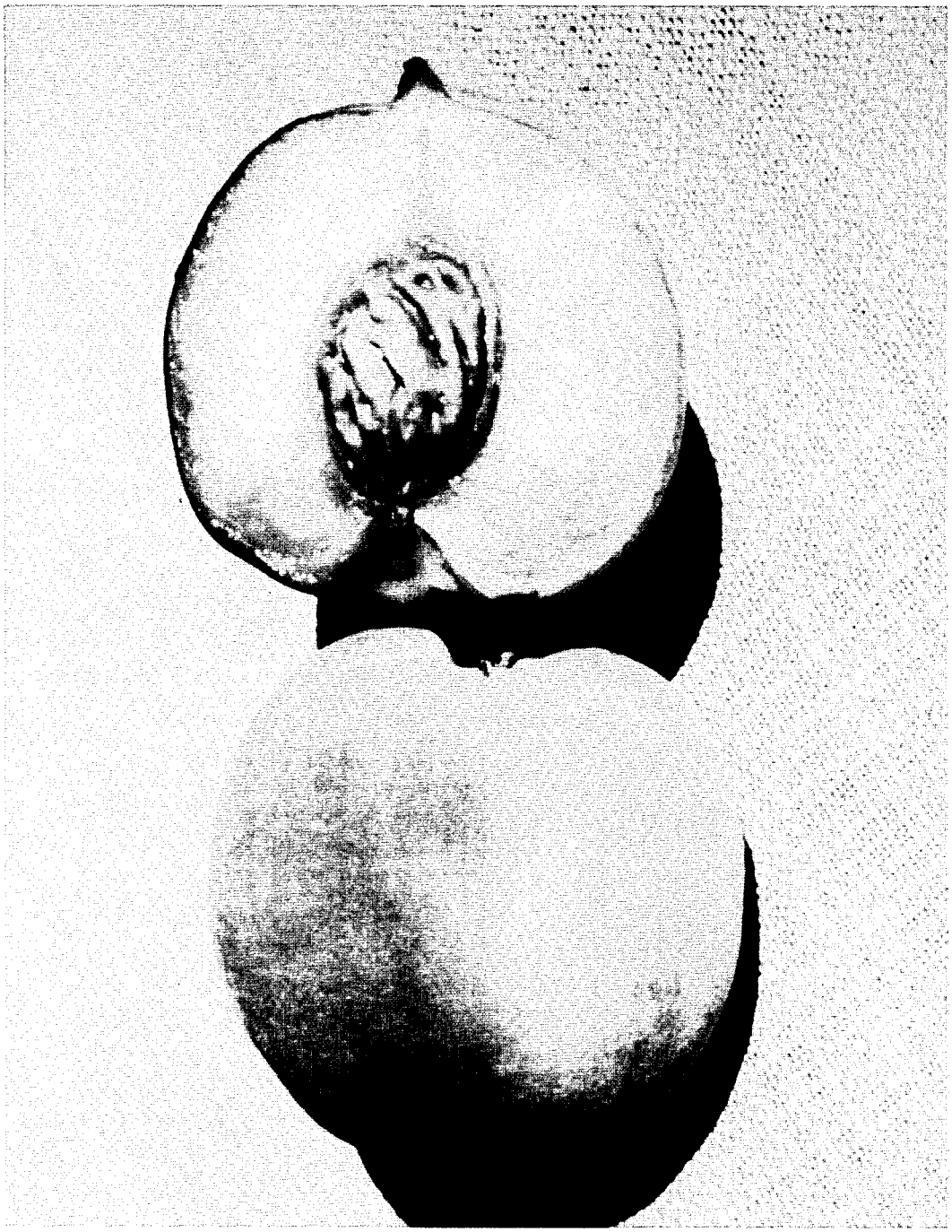
GRANT MERRILL
INVENTOR
Huebner & Worrel
ATTORNEYS

United States Patent Office

Plant Pat. 2,694
Patented Dec. 27, 1966

2,694
PEACH TREE

Grant Merrill, 416 N. Anderson Road,
Exeter, Calif. 25680

Filed June 11, 1965, Ser. No. 463,412
1 Claim. (Cl. Plt.—43)

The present invention relates to a peach tree and more particularly to a new and distinct variety thereof broadly characterized by vigorous and regular bearing; early bloom; and the production of early ripening, red-skinned firmly textured yellow-fleshed peaches.

The instant variety peach tree blooms at a time which is generally regarded as somewhat early, being about the same time as the July Elberta of U.S. Plant Patent No. 15. Its fruit ripens a few days earlies than the Merrill Gemfree of U.S. Plant Patent No. 1,409, which the instant variety most closely resembles. Its fruit distinguishes, however, from the Merrill Gemfree in providing a shallower, smaller lipped suture which presents a more uniformly smooth outer skin surface having a brighter red coloring. The flesh of the fruit of the instant variety is further distinguished from that of the Merrill Gemfree in its more brilliant yellow coloring with a minimum of red flecking when firm ripe, in having a better flavor, in having a more melting consistency when soft ripe, and in a reduced tendency to oxidize, or brown, when exposed to air. For a peach which ripens so early, it is remarkably freestone when picked firm ripe for commercial use and permitted to mature to a soft ripe condition during shipment.

I originated the present variety of peach tree on a farm formerly owned by me near Red Bluff, Tehama County, California. I first crossed a Merrill Goldrush peach tree (unpatented) with a Merrill Gemfree of U.S. Plant Patent No. 1,409. The seeds from this cross were propagated and produced a number of different varieties from which I selected the instant variety as providing the earliest ripening fruit. Buds from the new selected tree were budded into a number of Nemagard seedling peach trees (unpatented) at a nursery in Merced County, California in May 1962 and in the winter of 1962–63 transplanted into a test plot at Dinuba, Tulare County. The trees fruited in June 1964 and the fruit and tree characteristics resulting from such budding proved identical to those of the original tree.

The accompanying drawing is a dye transfer color print of a photograph of a soft ripe fruit of the subject variety which was permitted to ripen on the tree for true skin color and divided on its suture plane to reveal flesh coloration and pit characteristics.

Referring more specifically to the pomological details of this new and distinct variety of peach tree, the following has been observed under the ecological conditions prevailing at the test plot at Dinuba, Tulare County, California, and is an outlined description thereof. All major color plate identifications are by reference to the Nickerson Color Fan of the American Horticultural Council.

*Tree*

Size: Large, vigorous, with shape and density determined by pruning methods.
Trunk: Medium stocky, medium smooth.
Branches: Lenticels, numerous, medium sized.
Leaves (selected from midportion of vigorous unbranched terminal shoots 12″ to 18″ long):
- *Size.*—Large.
- *Length.*—5″ to 7″, average 6″.
- *Width.*—1¼″ to 1⅝″, average 1 7/16″.
- *Form.*—Lanceolate, tip acuminate, medium thick.

- *Color.*—Upper surface, dark yellowish green (10GY 4/5); under surface, moderate yellow green (5GY 5/6); midrib, under surface, vivid greenish yellow (7.5Y 8/12).
- *Class* (Meador & Blake: Proceedings of Am. Soc. Hor. Sc., vol. 37, page 206).—2 and 3.
- *Margin.*—Glandular, crenate.
- *Petiole.*—Medium long, medium slender.
- *Stipules.*—At base of leaf, falling off early.
- *Glands.*—Varying in number to five, mostly on petiole, some on base of leaves, reniform, light yellowish green.

Flower buds: Medium size, plump, pubescent.
Flowers: Generally early, medium size, dark pink. Pollen—abundant.

*Fruit*

Maturity when described, firm to soft ripe.
Size: Variable.
- *Axial diameter.*—2¼″ to 2⅝″, average 2 7/16″, under normal environmental and horticultural conditions with usual thinning to space fruit 6″ to 8″ on fruit bearing branches.
- *Transverse in suture plane.*—2⅜″ to 2¾″, average 2 9/16″.
- *At right angle to suture plane.*—2¼″ to 2¾″, average 2½″.

Form: Variable, generally globose, somewhat eliptical before maturity, has slight suture and apical point.
- *Suture.*—Distinct, has slight depression beyond pistil point.
- *Lips.*—Unequal, not pronounced.
- *Ventral surface.*—Rounded.
- *Cavity.*—Elongated in suture plane, suture showing on both sides.
- *Depth.*—¼″ to ½″, average ⅜″.
- *Breadth.*—Average ⅝″.
- *Markings.*—Under color yellow with some red blush and red striping.
- *Base.*—Retuse.
- *Apex.*—Mucronate, some cuspidate, pistil point apical.
- *Stem.*—Length, ¼″ to ⅜″, average 5/16″.
- *Diameter.*—3/32″ to 5/32″, average ⅛″.

Skin: Medium thick, medium tough, non astringent, tenacious to flesh, free in part when soft ripe.
- *Under color.*—Yellow (5Y 9/9) to (2.5Y 9/9) with strong reddish orange (7.5R 5/13) to dark red (5R 3/7) blush covering 50% to 90% of the surface.
- *Down.*—Scant, short, rolls up when rubbed.

Flesh:
- *Color.*—Brilliant yellow (5Y 9/9) to (5Y 8/12) to greenish yellow (10Y 9/9) near the pit, little or no red when firm ripe. Yellow red (5YR 9/4) to moderate orange-yellow (10YR 8/10) with some red flecking when soft ripe as shown in the drawing. Surface of pit cavity—brilliant greenish yellow (10Y 9/9) with occasionally some red when firm ripe. Brilliant yellow (5Y 9/9) when soft ripe.
- *Amygdalin.*—Moderate.
- *Juice.*—Abundant and rich when soft ripe.
- *Texture.*—Firm to soft, melting when ripe, resists oxidation when exposed to air and thus has low incidence of darkening because of exposure to air.
- *Fibers.*—Few and fine.
- *Ripens.*—Evenly.
- *Flavor.*—Vinous, rich, superior.
- *Aroma.*—Distinct, fragrant.
- *Eating quality.*—Superior.

Stone: Adheres to flesh when hard ripe, entirely free when soft ripe when permitted to ripen off the tree.

*Fibers.*—Short.

*Size.*—Generally small.

*Form.*—Generally oval to obovate, tip cuspidate.

*Base.*—Usually straight to slightly oblique.

*Hilum.*—Oval to round.

*Sides.*—Usually equal.

*Surface.*—Irregularly furrowed on ventral and dorsal edges, usually pitted in the center and toward base.

*Pits.*—Circular and elongated.

*Ventral edge.*—Thick, occasionally with wing toward base.

*Dorsal edge.*—Wide, with irregular grooves throughout.

*Color.*—Light brown.

Use: Fresh market, local and distant.

*Keeping quality.*—Good.

*Shipping quality.*—Good.

Although the new variety of peach tree possesses the described characteristics of the growing condition in Tehama County, California, having first been observed near Red Bluff, Tehama County, California at the northern end of the Sacramento Valley, and later confirmed at Dinuba in Tulare County, California in the central portion of the San Joaquin Valley, it is to be understood that variation of the usual magnitude in characteristics incident to the growing conditions, fertilization, pruning and pest control are to be expected.

Having thus described and illustrated my new variety of peach tree, what is claimed as new and desired to be secured by Letters Patent is:

A new and distinct variety of peach tree substantially as illustrated and described and which is characterized by its vigorous growth, its early blooming about the same time as the July Elberta of U.S. Plant Patent No. 15; and its regular and heavy bearing of freestone, red-skinned, firm textured, yellow fleshed peaches which ripen a few days earlier than the Merrill Gemfree of U.S. Plant Patent No 1,409 which it most nearly resembles but from which it is distinguished in its fruit having a more brilliant yellow colored flesh firm ripe which frees from the stone when soft ripe after being permitted to ripen off the tree, has superior flavor, softens into a more melting consistency when soft ripe and has greater resistance to oxidation when exposed to air.

No references cited.

ABRAHAM G. STONE, *Primary Examiner,*

R. E. BAGWILL, *Assistant Examiner.*